United States Patent
Otsuka et al.

(10) Patent No.: US 9,291,525 B2
(45) Date of Patent: *Mar. 22, 2016

(54) GAS SENSOR ELEMENT AND GAS SENSOR

(71) Applicant: NGK SPARK PLUG CO., LTD., Nagoya-shi, Aichi (JP)

(72) Inventors: Shigehiro Otsuka, Gifu (JP); Masaki Onkawa, Komaki (JP); Toru Iwano, Komaki (JP); Satoshi Teramoto, Nisshin (JP); Kuniharu Tanaka, Komaki (JP); Takeshi Mitsuoka, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 216 days.

This patent is subject to a terminal disclaimer.

(21) Appl. No.: 13/907,230

(22) Filed: May 31, 2013

(65) Prior Publication Data
US 2014/0130572 A1    May 15, 2014

(30) Foreign Application Priority Data
Nov. 13, 2012  (JP) ................. 2012-249600

(51) Int. Cl.
*G01N 27/407*  (2006.01)
*G01M 15/10*  (2006.01)

(52) U.S. Cl.
CPC ......... *G01M 15/102* (2013.01); *G01N 27/4077* (2013.01)

(58) Field of Classification Search
CPC .................................................. G01N 27/4077
See application file for complete search history.

(56) References Cited

U.S. PATENT DOCUMENTS

| 7,329,844 B2 | 2/2008 | Kojima et al. |
| 2012/0211362 A1 | 8/2012 | Onkawa et al. |
| 2014/0291150 A1* | 10/2014 | Otsuka et al. ........... 204/424 |

FOREIGN PATENT DOCUMENTS

| JP | 10-288593 A | 10/1998 |
| JP | 2003-322632 A | 11/2003 |
| JP | 2007-206082 A | 8/2007 |
| JP | 2009-080110 A | 4/2009 |
| JP | 2013-104706 A | 5/2013 |

OTHER PUBLICATIONS

Extended European Search Report dated Feb. 25, 2014 for corresponding European Patent Application No. 13170137.
International Search Report for PCT/IB2012/056552 dated Mar. 12, 2013.

* cited by examiner

*Primary Examiner* — Laura Martin
*Assistant Examiner* — Alex Devito
(74) *Attorney, Agent, or Firm* — Sughrue Mion, PLLC

(57) ABSTRACT

A gas sensor element and a gas sensor incorporating the gas sensor element. The gas sensor element (100) includes a detection portion (150) including a solid electrolyte body (105) and a pair of electrodes (104) and (106) disposed on the solid electrolyte body; and a porous protection layer (20) covering the detection portion. The porous protection layer includes an inner porous layer (21) and an outer porous layer (23). The inner porous layer has a higher porosity than the outer porous layer. Further, the inner porous layer contains, as main components, ceramic particles (21a), and ceramic fiber filaments (21b), and the amount of the ceramic fiber filaments is 25 to 75 vol % based on the total amount of the ceramic particles and the ceramic fiber filaments taken as 100 vol %.

2 Claims, 5 Drawing Sheets

GAS SENSOR ELEMENT AND GAS SENSOR

BACKGROUND OF THE INVENTION

1. Field of the Invention

The present invention relates to a gas sensor element and a gas sensor suitably employed for determining the concentration of a particular gas contained in, for example, combustion gas or exhaust gas of a combustor, an internal combustion engine, etc.

2. Description of the Related Art

Conventionally, a gas sensor is used for determining the concentration of a particular component (oxygen, etc.) in the exhaust gas of an internal combustion engine. The gas sensor has a gas sensor element provided therein. The gas sensor element has, on a forward end side thereof, a detection element including a solid electrolyte body and a pair of electrodes disposed on the solid electrolyte body. The gas sensor element may be exposed to poisoning substances (e.g., silicon and phosphorus) contained in exhaust gas and may suffer adhesion of water droplets contained in exhaust gas. Thus, in order to trap poisoning substances and to prevent direct contact of water droplets with the gas sensor element, the outer surface of the gas sensor element is covered with a porous protection layer. That is, the detection element, which is exposed to a gas-to-be-measured (exhaust gas), is entirely covered with the porous protection layer.

Also, the following technique has been developed: the porous protection layer is formed of two layers (i.e., an upper layer and a lower layer), and, by means of the lower layer having a porosity higher than that of the upper layer, an anchor effect brings the upper layer into close contact with the lower layer, whose surface is roughened by pores (see Patent Documents 1 and 2).

Patent Document 1: Japanese Patent Application Laid-Open (kokai) No. 2003-322632 (claim 15)

Patent Document 2: Japanese Patent Application Laid-Open (kokai) No. 2007-206082 (claim 15)

3. Problems to be Solved by the Invention

By employing the porous protection layer having a two-layer structure such that the lower layer has a higher porosity than the upper layer, the total volume of voids (empty spaces) contained in the lower layer increases, thereby imparting a thermal insulation property to the lower layer. Therefore, even when the upper layer is cooled by adhesion of water, the gas sensor element on the inner side is unlikely to be suddenly cooled. Even in a state where the detection element is heated by means of a heater, damage to the gas sensor element caused by adhesion of water can be effectively suppressed.

However, when the porosity of the porous layer is increased, a problem may arise in that the number of bonding sites between particles forming the porous layer is reduced, resulting in a layer of decreased strength. Meanwhile, a method has been proposed in which a porous layer is formed from particles having a smaller particle size (hereinafter the particles are also referred to as "fine particles") for the purpose of increasing the strength of the porous layer while maintaining the porosity of the porous layer at a high level. When the porous layer is formed from a slurry containing fine particles, the strength of the layer is increased, because of an increase in the number of bonding sites between particles. However, the amount of solvent is reduced while drying the slurry, and thus cracking is likely to occur in the layer due to separation of bonded fine particles by surface tension.

SUMMARY OF THE INVENTION

In view of the foregoing, an object of the present invention is to provide a gas sensor element in which cracking caused by adhesion of water is suppressed by covering the gas sensor element with two porous protection layers, and in which cracking is suppressed in an inner porous layer having higher porosity and increased strength. Another object of the present invention is to provide a gas sensor incorporating the gas sensor element.

The above object of the invention has been achieved by providing a gas sensor element which comprises a detection portion including a solid electrolyte body and a pair of electrodes disposed on the solid electrolyte body; and a porous protection layer covering the detection portion. In the gas sensor element, the porous protection layer comprises an inner porous layer provided over the detection portion, and an outer porous layer formed externally of the inner porous layer; the inner porous layer has a higher porosity than the outer porous layer; the inner porous layer contains, as main components, ceramic particles, and ceramic fiber filaments which are mainly formed of a ceramic material and which have a mean fiber length of 70 to 200 µm; and the amount of the ceramic fiber filaments is 25 to 75 vol % based on the total amount of the ceramic particles and the ceramic fiber filaments contained in the inner porous layers, the total amount taken as 100 vol %.

By employing an outer porous layer having a porosity lower than that of the inner porous layer, the outer porous layer having reduced porosity effectively traps poisoning substances and water droplets, and thus poisoning substances and water are unlikely to reach the detection portion. Furthermore, by employing the inner porous layer having a porosity higher than that of the outer porous layer, the total volume of voids (empty spaces) contained in the inner porous layer is increased, thereby imparting a thermal insulation property to the inner porous layer. Therefore, even when the outer porous layer is cooled by adhesion of water, the detection portion located on the inner side is unlikely to be suddenly cooled. Even in a state in which the detection portion is heated by means of a heater, damage to the gas sensor element caused by adhesion of water can be effectively suppressed.

Since the inner porous layer having a higher porosity contains, as main components, ceramic particles and ceramic fiber filaments which are mainly formed of a ceramic material, the inner porous layer can be toughened, and the strength of the layer can be increased. In addition, unlike the case where the inner porous layer is formed from fine particles, cracking in the inner porous layer can be prevented, which would otherwise occur due to separation of bonded fine particles by surface tension.

As used herein, the expression "the inner porous layer contains, as main components, ceramic particles, and ceramic fiber filaments which are mainly formed of a ceramic material" means that the total amount of the ceramic particles and the ceramic fiber filaments is 50 wt % or more of the material forming the inner porous layer. As used herein, the term "ceramic" means, for example, alumina, silica, spinel, zirconia, mullite, zircon, cordierite, silicon carbide, silicon nitride, titania, etc. The inner porous layer may contain a glass component, etc., in addition to ceramic particles and ceramic fiber filaments.

The ceramic fiber filaments have a mean fiber length of 70 to 200 µm, and the amount of the ceramic fiber filaments is 25 to 75 vol % based on the total amount of the ceramic particles and the ceramic fiber filaments, the total amount taken as 100 vol %. Therefore, the strength of the inner porous layer can be increased while the occurrence of cracking in the layer is suppressed. When the mean fiber length of the ceramic fiber filaments is less than 70 µm, suppression of cracking in the inner porous layer is insufficient, whereas when the mean fiber length of the ceramic fiber filaments exceeds 200 μm; i.e., when the length of the ceramic fiber filaments is excessively large, sintering of ceramic particles (interparticle bonding) in the inner porous layer is inhibited, whereby the strength of the layer may be lowered. Meanwhile, when the amount of the ceramic fiber filaments is less than 25 vol %, cracking in the inner porous layer is insufficiently suppressed, whereas when the amount of the ceramic fiber filaments exceeds 75 vol %; i.e., when the amount of the ceramic fiber filaments is excessively large, sintering of ceramic particles (interparticle bonding) in the inner porous layer is inhibited, whereby the strength of the layer may be lowered.

In a second aspect, the present invention provides (2) a gas sensor which comprises the sensor element as described in (1) above for determining the concentration of a particular gas component in a gas-to-be-measured, and a housing for holding the sensor element.

Effect of the Invention

According to the present invention, cracking of a gas sensor element caused by adhesion of water is suppressed by covering the gas sensor element with inner and outer porous protection layers. Further, cracking is suppressed in the inner porous layer having a higher porosity than the outer porous layer by introducing, into the inner porous layer ceramic particles and ceramic fiber filaments having the above characteristics as main components, whereby the strength of the inner porous layer can be increased.

DESCRIPTION OF REFERENCE NUMERALS

Figure 1:
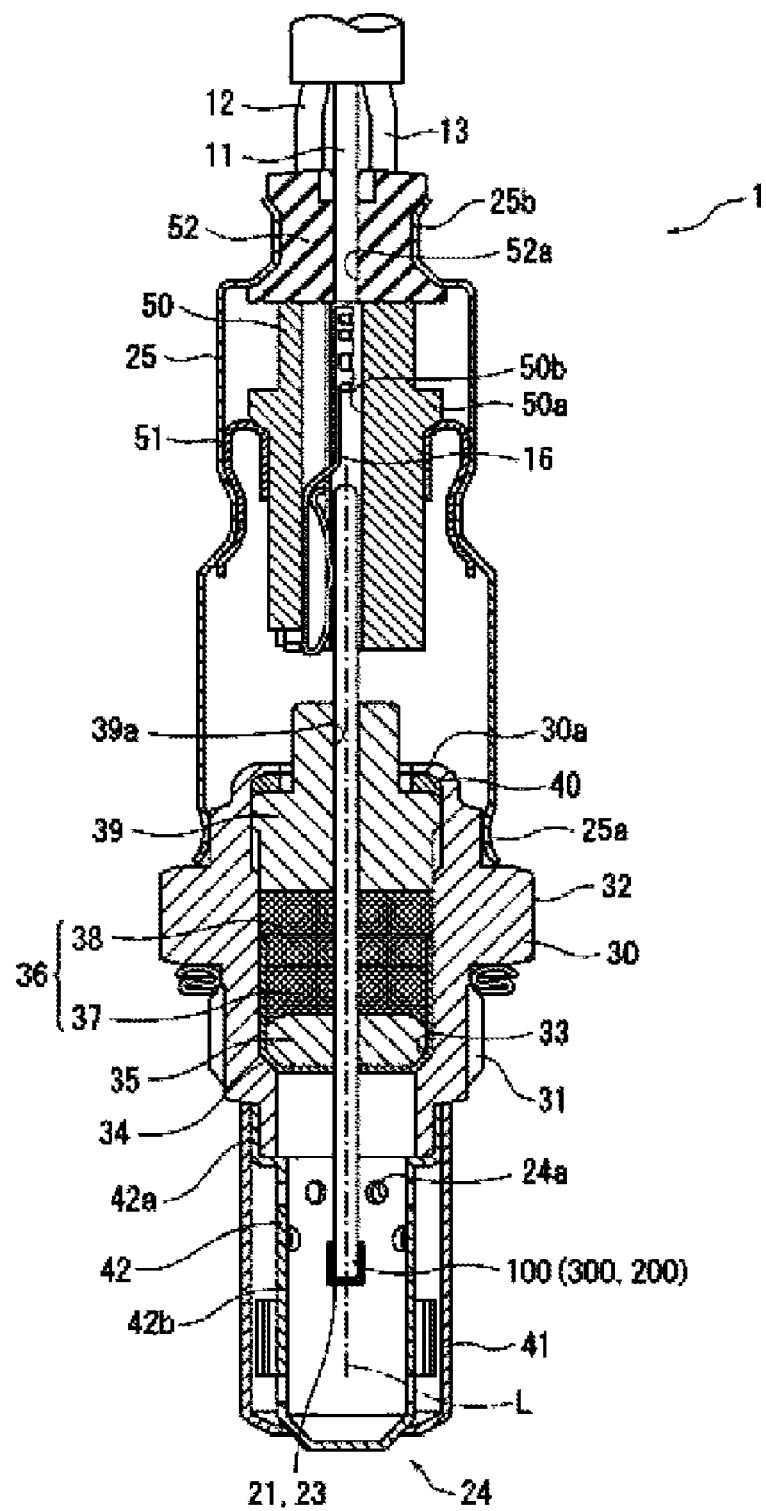
FIG. 1 is a sectional view of a gas sensor (oxygen sensor) according to a first embodiment of the present invention, taken along the longitudinal direction of the gas sensor.

Reference numerals used to identify various structural features in the drawings include the following.
1: gas sensor
20, 20C: porous protection layer
21, 21B, 21C: inner porous layer
21a: ceramic particle
21b: ceramic fiber filament
23, 23B, 23C: outer porous layer
30: housing
104, 106, 108, 110, 104C, 106C, 108C, 110C: a pair of electrodes
105, 105C, 109, 109C: solid electrolyte body
100, 100B, 100C: gas sensor element
150, 150B, 150C: detection portion
300, 300C: detection element
L: axis

DETAILED DESCRIPTION OF THE PREFERRED EMBODIMENTS

Preferred embodiments of the present invention will next be described with reference to the drawings. However, the present invention should not be construed as being limited thereto.

Figure 2:
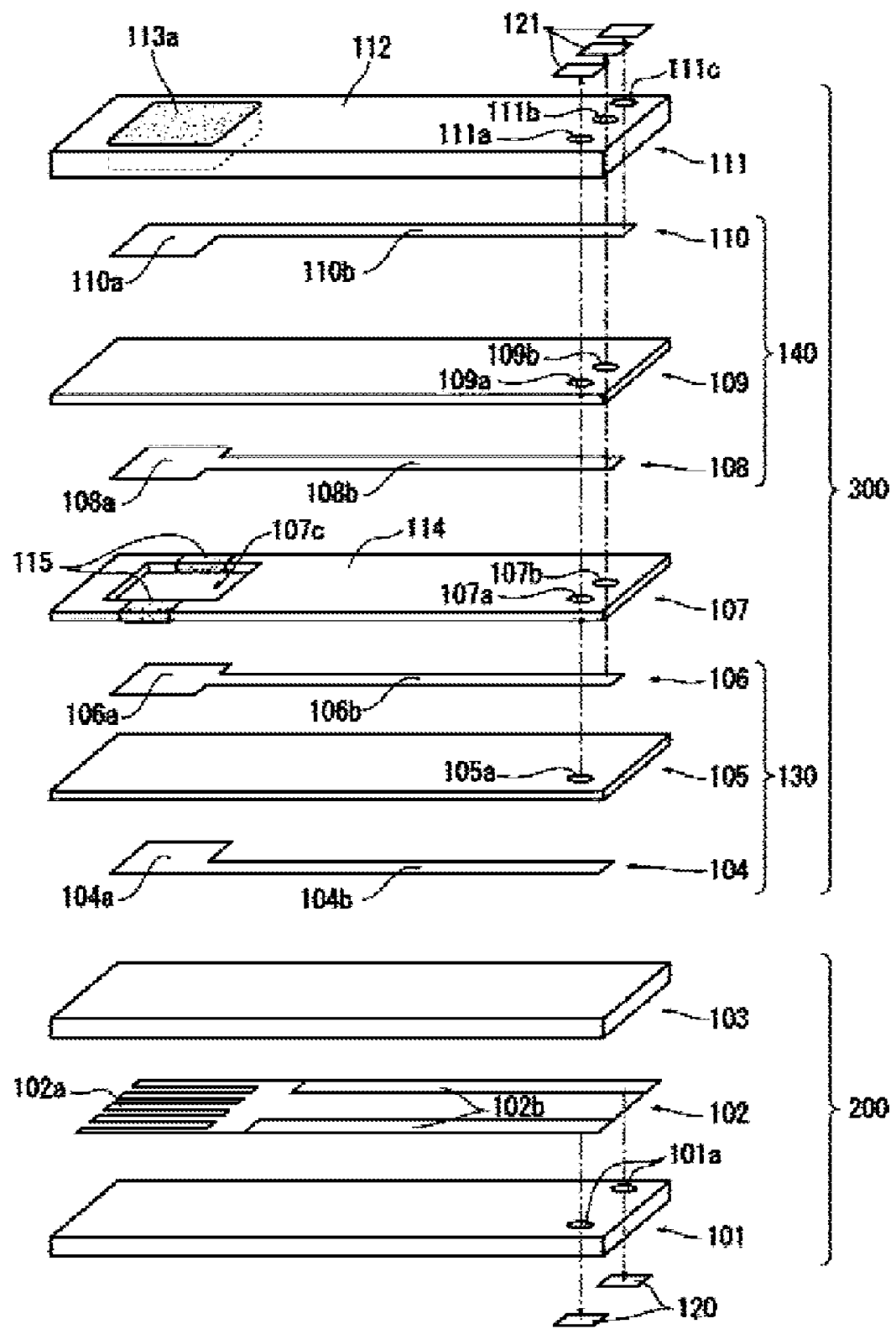
FIG. 2 is a schematic, exploded perspective view of a detection element and a heater.
Figure 3:
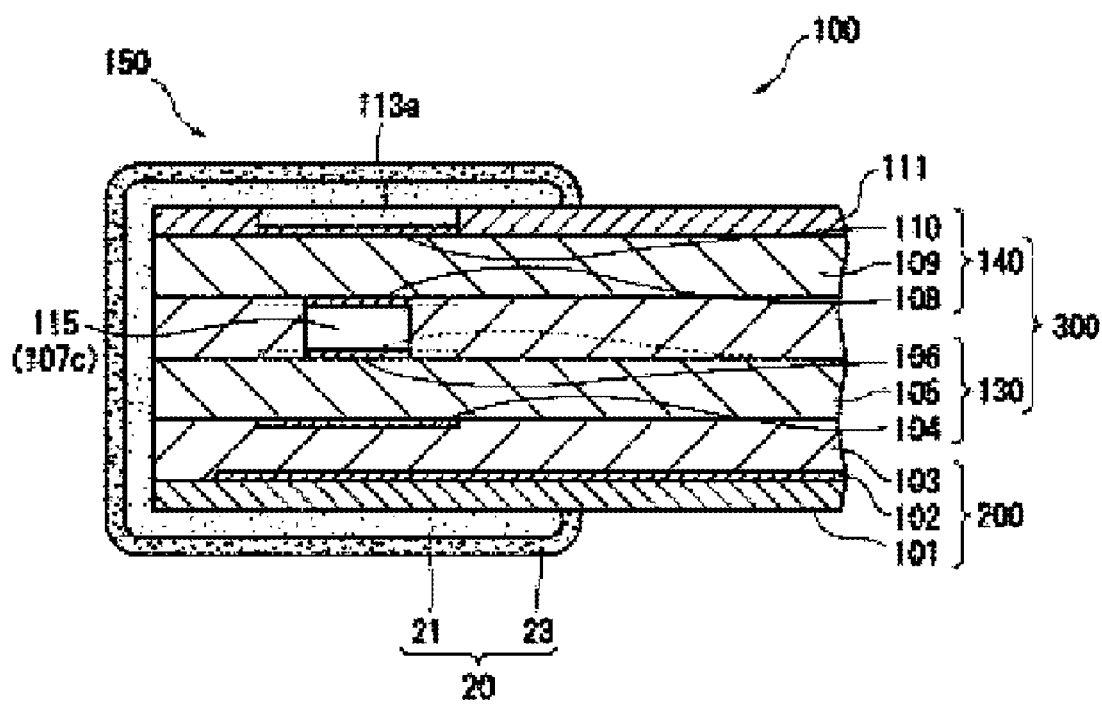
FIG. 3 is a fragmentary, enlarged sectional view of a forward end portion (detection portion) of the detection element shown in FIG. 1.

FIG. 1 is a sectional view of a gas sensor (oxygen sensor) 1 according to a first embodiment of the present invention, taken along the longitudinal direction of the gas sensor (the direction of an axis L). FIG. 2 is a schematic, exploded perspective view of a detection element 300 and a heater 200. FIG. 3 is a sectional view of the detection element 300 taken orthogonally to the direction of the axis L.

As shown in FIG. 1, the gas sensor 1 includes a gas sensor element 100 composed of the detection element 300 and the heater 200 laminated on the detection element 300; a metallic shell (corresponding to the "housing" of the invention) 30 for holding the gas sensor element 100, etc., therein; and a protector 24 attached to a forward end portion of the metallic shell 30. The gas sensor element 100 is disposed so as to extend in the direction of the axis L.

As shown in FIG. 2, the heater 200 includes a first substrate 101 and a second substrate 103, which predominantly contain alumina, and a heat-generating element 102, which is sandwiched between the first substrate 101 and the second substrate 103 and predominantly contains platinum. The heat-generating element 102 has a heat-generating portion 102a located at the forward end thereof and a pair of heater lead portions 102b extending from the heat-generating portion 102a along the longitudinal direction of the first substrate 101. The ends of the heater lead portions 102b are electrically connected to corresponding heater-side pads 120 via conductors formed in heater-side through holes 101a provided in the first substrate 101.

The detection element 300 includes an oxygen concentration determination cell 130 and an oxygen pump cell 140. The oxygen concentration determination cell 130 includes a first solid electrolyte body 105, and a first electrode 104 and a second electrode 106, which are formed on the respective opposite sides of the first solid electrolyte body 105. The first electrode 104 includes a first electrode portion 104a and a first lead portion 104b extending from the first electrode portion 104a along the longitudinal direction of the first solid electrolyte body 105. The second electrode 106 includes a second electrode portion 106a and a second lead portion 106b extending from the second electrode portion 106a along the longitudinal direction of the first solid electrolyte body 105.

The first electrode 104 and the second electrode 106 correspond to "a pair of electrodes" of the invention.

The end of the first lead portion 104b is electrically connected to a corresponding detection-element-side pad 121 via conductors formed respectively in a first through hole 105a provided in the first solid electrolyte body 105, a second through hole 107a provided in an insulation layer 107 described below, a fourth through hole 109a provided in a second solid electrolyte body 109, and a sixth through hole 111a provided in a protection layer 111. The end of the second lead portion 106b is electrically connected to a corresponding detection-element-side pad 121 via conductors formed respectively in a third through hole 107b provided in the insulation layer 107 described below, a fifth through hole 109b provided in the second solid electrolyte body 109, and a seventh through hole 111b provided in the protection layer 111.

Meanwhile, the oxygen pump cell 140 includes a second solid electrolyte body 109, and a third electrode 108 and a fourth electrode 110, which are formed on respective opposite sides of the second solid electrolyte body 109. The third electrode 108 includes a third electrode portion 108a and a third lead portion 108b extending from the third electrode portion 108a along the longitudinal direction of the second solid electrolyte body 109. The fourth electrode 110 includes a fourth electrode portion 110a and a fourth lead portion 110b extending from the fourth electrode portion 110a along the longitudinal direction of the second solid electrolyte body 109.

The third electrode 108 and the fourth electrode 110 correspond to "a pair of electrodes" of the invention.

The end of the third lead portion 108b is electrically connected to a corresponding detection-element-side pad 121 via conductors formed respectively in the fifth through hole 109b provided in the second solid electrolyte body 109 and the seventh through hole 111b provided in the protection layer 111. Meanwhile, the end of the fourth lead portion 110b is electrically connected to a corresponding detection-element-side pad 121 via a conductor formed in an eighth through hole 111c provided in the protection layer 111, described below. The second lead portion 106b and the third lead portion 108b have the same electric potential.

The first solid electrolyte body 105 and the second solid electrolyte body 109 are partially-stabilized-zirconia sintered bodies which are formed by adding yttria ($Y_2O_3$) or calcia (CaO) serving as a stabilizer to zirconia ($ZrO_2$).

The heat-generating element 102, the first electrode 104, the second electrode 106, the third electrode 108, the fourth electrode 110, the heater-side pads 120, and the detection-element-side pads 121 may be formed from a platinum group element. Platinum group elements which are preferred for forming these components include Pt, Rh, Pd, etc. These elements may be employed singly or in combination of two or more thereof.

In view of heat resistance and resistance to oxidation, more preferably, Pt is predominantly used to form the heat-generating element 102, the first electrode 104, the second electrode 106, the third electrode 108, the fourth electrode 110, the heater-side pads 120, and the detection-element-side pads 121. Furthermore, preferably, the heat-generating element 102, the first electrode 104, the second electrode 106, the third electrode 108, the fourth electrode 110, the heater-side pads 120, and the detection-element-side pads 121 contain a ceramic component in addition to a main component of a platinum group element(s). In view of attachment in a fixed condition, preferably, the ceramic component is similar to a material which is predominantly contained in a counterpart of the laminate (e.g., a main component of the first solid electrolyte body 105 and the second solid electrolyte body 109).

The insulation layer 107 is formed between the oxygen pump cell 140 and the oxygen concentration determination cell 130. The insulation layer 107 includes an insulation portion 114 and a diffusion resistor 115. The insulation portion 114 of the insulation layer 107 has a hollow measuring chamber 107c formed at a position corresponding to the second electrode portion 106a and the third electrode portion 108a. The measuring chamber 107c communicates with the ambient atmosphere along the lateral direction of the insulation layer 107. In the communication region of the insulation layer 107, the diffusion resistor 115 is disposed so as to establish gas diffusion at a predetermined flow rate between the ambient atmosphere and the measuring chamber 107c.

No particular limitation is imposed on the insulation portion 114, so long as the insulation portion 114 is formed of an electrically insulative ceramic sintered body. Examples of such a ceramic sintered body include oxide ceramics, such as alumina mullite, etc.

The diffusion resistor 115 is formed of a porous body of alumina. The diffusion resistor 115 controls the flow rate of a gas-to-be-measured into the measuring chamber 107c.

The protection layer 111 is formed on the surface of the second solid electrolyte body 109 such that the fourth electrode 110 is sandwiched therebetween. The protection layer 111 includes a porous electrode protection portion 113a, which covers the fourth electrode portion 110a for protecting the fourth electrode portion 110a from poisoning, and a reinforcement portion 112, which covers the second solid electrolyte body 109 for protecting the second solid electrolyte body 109, with the fourth lead portion 110b sandwiched therebetween. The gas sensor element 100 of the present embodiment corresponds to an oxygen sensor element which functions as follows: the direction and magnitude of current flowing between the electrodes of the oxygen pump cell 140 are adjusted such that a voltage (electromotive force) generated between the electrodes of the oxygen concentration determination cell 130 has a predetermined value (e.g., 450 mV), and the oxygen concentration in a gas-to-be-measured is linearly determined according to current flowing in the oxygen pump cell 140.

Referring back to FIG. 1, the metallic shell 30 is made of SUS430 and includes an externally threaded portion 31 adapted to mount the gas sensor to an exhaust pipe, and a hexagonal portion 32 to which a mounting tool is fitted in mounting the gas sensor. The metallic shell 30 further includes a shell-side stepped portion 33, which projects radially inward. The shell-side stepped portion 33 supports a metal holder 34 for holding the gas sensor element 100. The metal holder 34 holds therein a ceramic holder 35 and a talc 36 disposed in this order in the rearward direction. The talc 36 is composed of a first talc 37 disposed within the metal holder 34, and a second talc 38 disposed in and outside the rear end of the metal holder 34. The first talc 37 is compressively charged into the metal holder 34, thereby fixing the gas sensor element 100 in relation to the metal holder 34. Also, the second talc 38 is compressively charged into the metallic shell 30, thereby ensuring a seal between the outer surface of the gas sensor element 100 and the inner surface of the metallic shell 30. A sleeve 39 made of alumina is disposed on the rear side of the second talc 38. The sleeve 39 is formed into a multi-stepped cylindrical shape and has an axial hole 39a extending along the axis. The gas sensor element 100 extends through the axial hole 39a. A rear-end crimp portion 30a of the metallic shell 30 is bent inward, thereby pressing the sleeve 39 toward the forward end of the metallic shell 30 via a ring member 40 made of stainless steel.

A protector 24 made of metal and having a plurality of gas intake holes 24a is welded to the outer circumferential surface of a forward end portion of the metallic shell 30 and covers a forward end portion of the gas sensor element 100 projecting from the forward end of the metallic shell 30. The protector 24 has a dual structure consisting of a closed-bottomed cylindrical outer protector 41 having a fixed outside diameter and a closed-bottomed cylindrical inner protector 42 disposed within the outer protector 41 and formed such that its rear end portion 42a is greater in outside diameter than its forward portion 42b.

Meanwhile, a forward end portion of a tubular sheath 25 made of SUS430 is fitted to a rear end portion of the metallic shell 30. The tubular sheath 25 is fixed to the metallic shell 30 by joining its diameter-expanded forward portion 25a to the metallic shell 30 by, for example, laser welding. A separator 50 is disposed within a rear portion of the tubular sheath 25. A holding member 51 intervenes between the separator 50 and the tubular sheath 25. The holding member 51 is engaged with a flange portion 50a of the separator 50 and is fixed between the tubular sheath 25 and the separator 50 by crimping the tubular sheath 25.

The separator 50 has a through hole 50b extending therethrough between its forward end and rear end for allowing insertion of lead wires 11 to 15 associated with the detection element 300 and the heater 200 (the lead wires 14 and 15 are not shown). The through hole 50b accommodates connection terminals 16 for connecting the lead wires 11 to 15 to the detection-element-side pads 121 of the detection element 300 and to the heater-side pads 120 of the heater 200. The lead wires 11 to 15 are connected to unillustrated external connectors. Electrical signals are transmitted between the lead wires 11 to 15 and external equipment, such as an ECU, via the connectors. Although unillustrated in detail, the lead wires 11 to 15 have a structure in which a conductor is covered with an insulation film made of resin.

Furthermore, a generally circular columnar rubber cap 52 is disposed on the rear side of the separator 50, for closing a rear end opening 25b of the tubular sheath 25. The rubber cap 52 fitted into the tubular sheath 25 is fixed to the tubular sheath 25 as follows: in a state where the rubber cap 52 is fitted into the rear end of the tubular sheath 25, the tubular sheath 25 is crimped radially inward along its outer circumference. The rubber cap 52 also has through holes 52a extending therethrough between its forward end and rear end for allowing the lead wires 11 to 15 to extend through the respective through holes 52a.

Next a porous protection layer 20 (an inner porous layer 21 and an outer porous layer 23) will be described, which is a feature of the present invention.

FIG. 3 is a fragmentary, enlarged sectional view of a forward end portion of the gas sensor element 100 shown in FIG. 1. The inner porous layer 21 is provided directly on the surface of a laminate of the detection element 300 and the heater 200, and the outer porous layer 23 is formed so as to cover the outer surface of the inner porous layer 21. That is, the porous protection layer 20 is provided so as to entirely cover the detection portion 150 located at a forward end portion of the gas sensor element 100.

Figure 7:
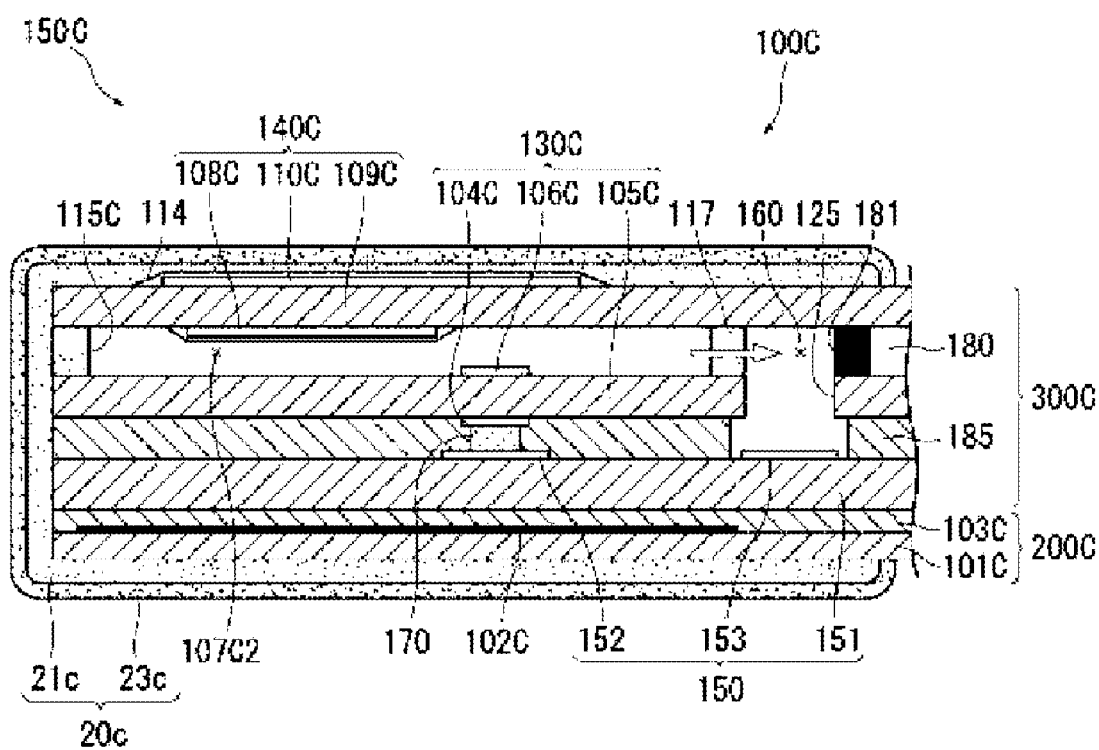
FIG. 7 is a sectional view of a gas sensor element, taken along the longitudinal direction of the gas sensor element, in a gas sensor ($NO_X$ sensor) according to a second embodiment of the present invention.

The detection portion 150 includes the detection element 300, and the detection element 300 includes the electrode portions (the first electrode portion 104a, the second electrode portion 106a, the third electrode portion 108a, and the fourth electrode portion 110a shown in FIG. 2, or a first electrode 104C, a second electrode 106C, a third electrode 108C, a fourth electrode 110C, a fifth electrode 152, and a sixth electrode 153 shown below in FIG. 7); the solid electrolyte bodies, each being sandwiched between the corresponding electrode portions (the first solid electrolyte body 105 and the second solid electrolyte body 109 shown in FIG. 2, or a first solid electrolyte body 105C, a second solid electrolyte body 109C, and a third solid electrolyte body 151 shown below in FIG. 7); and the measuring chamber (the measuring chamber 107c shown in FIG. 2, or a first measuring chamber 107c2 shown in FIG. 7). The porous protection layer 20 covers the detection element 300. When the detection element 300 and the heater 200 together form a laminate as in the case of the first embodiment, the porous protection layer 20 covers the laminate including the detection element 300 (i.e., a forward end portion of the gas sensor element 100).

Meanwhile, when the gas sensor element 100 does not include the heater 200, the porous protection layer 20 may be provided so as to entirely cover the detection element 300 (the detection portion 150).

Figure 4:
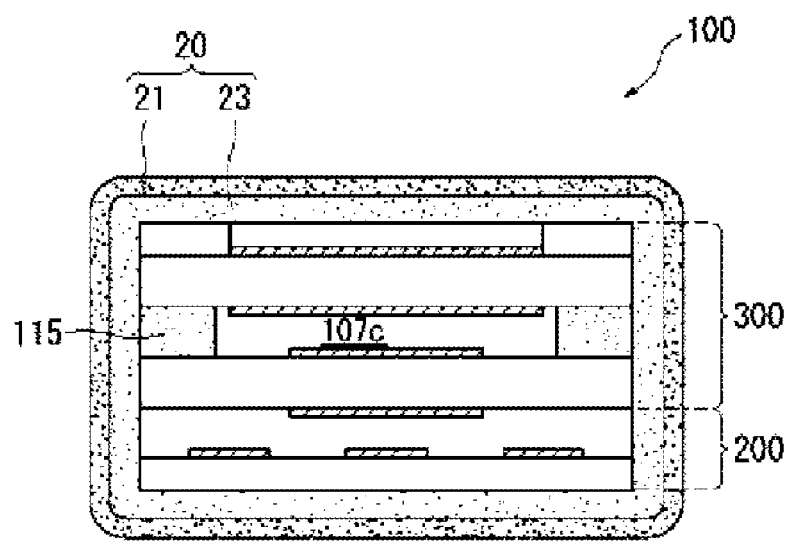
FIG. 4 is a schematic sectional view of a gas sensor element taken orthogonally to the direction of the axis.

The porous protection layer 20 is formed so as to cover the forward end surface of the gas sensor element 100 and extend rearward along the direction of the axis L while completely covering four surfaces (i.e., the front and back surfaces and the opposite side surfaces) of the gas sensor element 100 (laminate) (see FIG. 4).

FIG. 4 is a schematic sectional view, taken orthogonally to the direction of the axis L, of the gas sensor element 100 including the inner porous layer 21 and the outer porous layer 23.

The porosity of the inner porous layer 21 is higher than that of the outer porous layer 23. In order to allow gas permeation, pores formed in the inner porous layer 21 and the outer porous layer 23 are present in a three-dimensional network structure.

Thus, by providing the outer porous layer 23 having a porosity lower than that of the inner porous layer 21, the outer porous layer 23 having a reduced porosity effectively traps poisoning substances and water droplets, and thus poisoning substances and water are unlikely to reach the detection element 300 (the detection portion 150). In addition, by providing the inner porous layer 21 having porosity higher than that of the outer porous layer 23, the total volume of voids (empty spaces) contained in the inner porous layer 21 is increased, thereby imparting a thermal insulation property to the inner porous layer 21. Therefore, even when the outer porous layer 23 is cooled by adhesion of water, the detection portion 150 located on the inner side is unlikely to be suddenly cooled. Even in a state where the detection portion 150 is heated by means of the heater 200, damage to the gas sensor element 100 caused by adhesion of water can be effectively suppressed.

However, when the porosity of the inner porous layer 21 is increased, the strength of the layer is likely to be lowered as described above. When the inner porous layer 21 is formed from fine particles for improving the strength of the layer, cracking is likely to occur during formation of the layer.

Figure 5:
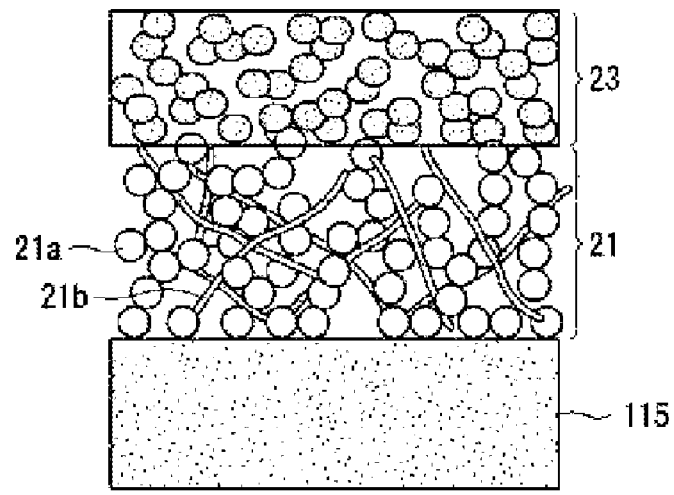
FIG. 5 schematically shows a cross section of the structure of an inner porous layer.

Therefore, as shown in FIG. 5, when the inner porous layer 21 contains, as main components, ceramic particles 21a and ceramic fiber filaments 21b (i.e., fiber filaments mainly formed of a ceramic material) having a mean fiber length of 70 to 200 μm, the strength of the inner porous layer 21 can be increased while cracking is suppressed. Conceivably, this is attributed to the fact that the inner porous layer 21 is toughened by means of the ceramic fiber filaments 21b incorporated into the inner porous layer 21, and thus the strength of the layer is enhanced. In addition, unlike the case where the inner porous layer 21 is formed from fine particles, cracking in the layer can be prevented, which would otherwise occur due to separation of bonded fine particles by surface tension. Since fiber generally has a thermal conductivity lower than that of powder (particles), the inner porous layer 21 exhibits a further increased thermal insulation property. Therefore, delay of the activation time of the gas sensor, which would otherwise occur by formation of the porous protection layer 20, can be reduced. The ceramic fiber filaments 21b correspond to fibrous particles having a diameter of 3 to 5 μm.

The amount of the ceramic fiber filaments 21b contained in the inner porous layer 21 is adjusted to 25 to 75 vol % based on the total amount of the ceramic particles and the ceramic fiber filaments contained in the inner porous layer, the total amount being taken as 100 vol %. When the amount of the ceramic fiber filaments 21b contained in the inner porous layer 21 is less than 25 vol %, cracking in the inner porous layer is insufficiently suppressed, whereas when the amount of the ceramic fiber filaments 21b exceeds 75 vol %; i.e., when the amount of the ceramic fiber filaments 21b is excessively large, sintering of the ceramic particles 21a (interparticle bonding) in the inner porous layer 21 is inhibited, whereby the strength of the inner porous layer 21 may be lowered.

The amount of the ceramic particles 21a or the ceramic fiber filaments 21b is determined as follows. Firstly, a scanning electron microscope image of a cross section of the inner porous layer 21 is obtained. Among ceramic fiber filaments 21b included in a plurality of regions of the image, ceramic fiber filaments 21b1 having a maximum fiber length LMax are selected. When ceramic fiber filaments 21b having the maximum fiber length LMax included in each of the aforementioned regions are out of the region, the region is enlarged so that all the ceramic fiber filaments 21b are included in the region. The vertical and horizontal dimensions of the region enlarged so that the ceramic fiber filaments 21b1 having the maximum fiber length LMax are included therein are also employed as vertical and horizontal dimensions of each of the other regions. The amount of the ceramic particles 21a or the ceramic fiber filaments 21b included in each of the regions is determined, and the thus-determined amounts of the ceramic particles 21a or the ceramic fiber filaments 21b included in all the regions are averaged.

Meanwhile, the mean fiber length of the ceramic fiber filaments 21b is adjusted to 70 to 200 µm. When the mean fiber length of the ceramic fiber filaments 21b is less than 70 µm, cracking in the inner porous layer is insufficiently suppressed, whereas when the mean fiber length exceeds 200 µm; i.e., when the length of the ceramic fiber filaments 21b is excessively large, sintering of the alumina particles 21a (interparticle bonding) in the inner porous layer 21 is inhibited, whereby the strength of the inner porous layer 21 may be lowered.

The mean fiber length of the ceramic fiber filaments 21b is determined as follows. Firstly, a scanning electron microscope image of a cross section of the inner porous layer 21 is obtained. Among ceramic fiber filaments 21b included in a plurality of regions of the image, ceramic fiber filaments 21b1 having the maximum fiber length LMax are selected. When ceramic fiber filaments 21b having the maximum fiber length LMax included in each of the aforementioned regions are out of the region, the region is enlarged so that all the ceramic fiber filaments 21b are included in the region, and then LMax is determined. Among a plurality of ceramic fiber filaments 21b included in each of the aforementioned regions, ceramic fiber filaments 21b having a fiber length of LMax/2 or more are selected, and the mean fiber length of the thus-selected ceramic fiber filaments 21b (including ceramic fiber filaments 21b1) is determined.

The smaller the particle size of the ceramic particles 21a contained in the inner porous layer 21, the greater the strength of the layer. Therefore, the mean particle size of the ceramic particles 21a is preferably 0.1 to 1.0 µm. When the mean particle size of the ceramic particles 21a is less than 0.1 µm, handling of the particles may become difficult, whereas when the mean particle size exceeds 1.0 µm, the strength of the layer may fail to be sufficiently improved.

The ceramic fiber filaments 21b may be, for example, ceramic fiber filaments formed of one or more species selected from the group consisting of alumina, silica, spinel, zirconia, mullite, zircon, cordierite, silicon carbide, silicon nitride, and titania.

The ceramic particles 21a may be, for example, ceramic particles formed of one or more species selected from the group consisting of alumina, silica, spinel, zirconia, mullite, zircon, cordierite, silicon carbide, silicon nitride, and titania.

The inner porous layer 21 may be formed by bonding together the aforementioned ceramic particles 21a and ceramic fiber filaments 21b through application of a slurry containing the ceramic particles 21a and ceramic fiber filaments 21b by, for example, a dipping process, a printing process, or a spraying process, followed by firing. By sintering the slurry containing the ceramic particles 21a, pores can be formed in the framework of the layer. Preferably, a slurry containing the aforementioned particles and a burning-off-type pore-forming material is sintered. This is because the pore-forming material burns off to leave pores, and the inner porous layer 21 exhibits high porosity. Examples of the pore-forming material which may be employed include carbon, resin beads, and organic or inorganic binder particles.

Preferably, the porosity of the inner porous layer 21 determined through image analysis, described below, is adjusted to 50 to 75%, since the aforementioned thermal insulation effect is readily obtained. When the porosity of the inner porous layer 21 is less than 50%, the gas diffusion resistance of the inner porous layer 21 tends to increase, whereas when the porosity of the inner porous layer 21 exceeds 75%, layer production may become difficult.

The inner porous layer 21 preferably has a thickness of 20 to 800 µm.

The outer porous layer 23 may be formed by, for example, bonding together, through firing or the like, particles of one or more ceramic materials selected from the group consisting of alumina, spinel, zirconia, mullite, zircon, and cordierite. By sintering a slurry containing the particles, pores are formed in the framework of the layer, in gaps among ceramic particles and as a result of burning off of an organic or inorganic binder contained in the slurry.

Preferably, the porosity of the outer porous layer 23 determined through image analysis, described below, is adjusted to 30 to 50%, since a barrier property to poisoning substances or water droplets is ensured without deteriorating gas permeability. When the porosity of the outer porous layer 23 is less than 30%, poisoning substances are apt to cause clogging, whereas when the porosity of the outer porous layer 23 exceeds 50%, water may penetrate into the outer porous layer 23, which may result in deteriorating resistance to adhesion of water.

The outer porous layer 23 preferably has a thickness of 100 to 800 µm.

The porosity of the inner porous layer 21 or the outer porous layer 23 is determined as follows.

Firstly, a micrograph (SEM image) of a cross section of the inner porous layer 21 or the outer porous layer 23 is binarized at a plurality of positions by means of commercially available image analysis software, and the percentage of black portions on the micrographed cross section is determined. Black portions on the micrographed cross section correspond to pores, and white portions correspond to the framework of the layer. Thus, the greater the occupancy of black portions, the higher the porosity.

Porosities determined through image analysis carried out at the plurality of positions on the micrographed cross section of the inner porous layer 21 or the outer porous layer 23 are averaged, to thereby determine the porosity of each layer.

In the first embodiment, both the inner porous layer 21 and the outer porous layer 23 entirely cover a forward end portion of the laminate. Since the inner porous layer 21 has a higher porosity than the outer porous layer 23, by the inner porous layer 21 entirely covering a forward end portion of the laminate of the detection element 300 and the heater 200, the total volume of voids in the inner porous layer 21, which is located on the laminate side, is further increased. As a result, thermal insulation performance is further improved. Thus, even when the outer porous layer 23 is cooled by adhesion of water, the gas sensor element 100 is unlikely to be suddenly cooled. Therefore, even in a state where the detection portion 150 is heated by the heater 200, damage to the gas sensor element 100 caused by adhesion of water can be more effectively suppressed.

Another porous layer may be provided between the inner porous layer 21 and the outer porous layer 23. Alternatively, another porous layer may be provided externally of the outer porous layer 23.

The inner porous layer 21 and the outer porous layer 23 may be produced through the following method: slurries which are to become the inner porous layer 21 and the outer porous layer 23 are sequentially applied by, for example, a dipping process, followed by sintering. In this case, after application and sintering of the slurry which is to become the inner porous layer 21, the slurry which is to become the outer porous layer 23 may be applied and sintered. Alternatively, the slurries which are to become the inner porous layer 21 and the outer porous layer 23 are sequentially applied, followed by a batch sintering process.

The thermal spraying process, the printing process, or the spraying process may be employed for producing the inner porous layer 21 and the outer porous layer 23. Alternatively, the inner porous layer 21 and the outer porous layer 23 may be formed by respectively different processes selected from among the dipping, thermal spraying, and spraying.

Figure 6:
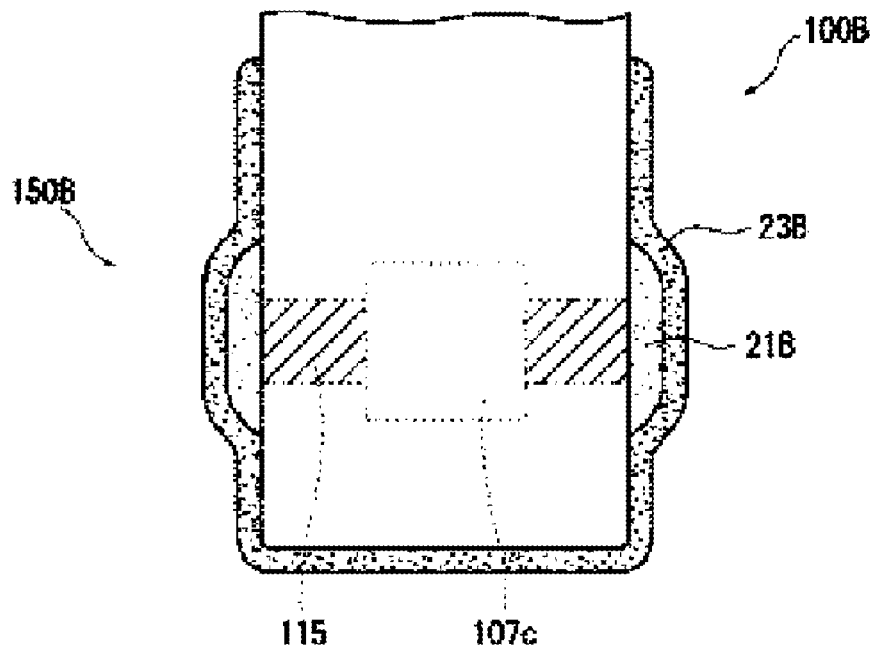
FIG. 6 is a sectional view of a modification of the gas sensor element of the first embodiment, taken along the longitudinal direction of the gas sensor element.

FIG. 6 shows a modification of the gas sensor element 100 of the first embodiment. In a gas sensor element 100B of FIG. 6, since a detection element and a heater are similar to those (the oxygen sensor element in FIG. 2) of the first embodiment, a description thereof is omitted.

In the gas sensor element 100B, an inner porous layer 21B does not entirely cover a forward end portion of the laminate, but covers only the diffusion resistor 115 and its periphery. Meanwhile, an outer porous layer 23B entirely covers the forward end portion of the laminate. Also in the example of FIG. 6, since the inner porous layer 21B has a higher porosity than the outer porous layer 23B, the outer porous layer 23B having a reduced porosity effectively traps poisoning substances and water droplets, and thus poisoning substances and water are unlikely to reach the detection element (the detection portion 150B). Furthermore, by means of the inner porous layer 21B having a porosity higher than that of the outer porous layer 23B, the total volume of voids (empty spaces) contained in the inner porous layer 21B is increased, thereby imparting a thermal insulation property to the inner porous layer 21B. Therefore, even when the outer porous layer 23B is cooled by adhesion of water, the detection element 300 located on the inner side is unlikely to be suddenly cooled. Even in a state where the detection portion 150B is heated by the heater 200, damage to the gas sensor element 100 caused by adhesion of water can be effectively suppressed.

Since the inner porous layer 21B contains, as main components, the aforementioned ceramic particles and ceramic fiber filaments which are mainly formed of a ceramic material, the strength of the inner porous layer 21B can be enhanced. In addition, unlike the case where the inner porous layer 21B is formed only from fine particles, cracking in the inner porous layer 21B can be prevented, which would otherwise occur due to separation of bonded fine particles by surface tension.

Next, a gas sensor ($NO_X$ sensor) according to a second embodiment of the present invention will be described with reference to FIG. 7. The gas sensor according to the second embodiment is similar to the gas sensor according to the first embodiment except for the configurations of a gas sensor element 100C, an inner porous layer 21C, and an outer porous layer 23C. Thus, the description and illustration of the metallic shell for holding the gas sensor element 100C, and like components are omitted.

The gas sensor element ($NO_X$ sensor element) 100C has a narrow, elongated plate shape and a structure in which three plate-like solid electrolyte bodies 109C, 105C, and 151 are arranged in layers while insulators 180 and 185 made of, for example, alumina are individually sandwiched therebetween. The laminate structure serves as a detection element 300C. A heater 200C is provided on the outer side (opposite the solid electrolyte layer 105C in FIG. 7) of the solid electrolyte body 151. The heater 200C is configured such that a heater pattern 102C formed predominantly from Pt is sandwiched between sheet-like insulation layers 103C and 101C formed predominantly from alumina.

The solid electrolyte bodies 109C, 105C, and 151 are formed from zirconia, which is a solid electrolyte, and has oxygen ion conductivity.

The detection element 300C includes a first pump cell (Ip1 cell) 140C, an oxygen-concentration determination cell (Vs cell) 130C, and a second pump cell (Ip2 cell) 150C, which are described below.

The first pump cell 140C includes the second solid electrolyte body 109C, and a third electrode 108C and a fourth electrode 110C formed respectively on the opposite surfaces of the second solid electrolyte body 109C. A porous protection layer 114 formed of a ceramic material is provided on the surface of the fourth electrode 110C for protecting the fourth electrode 110C against deterioration caused by exposure to a poisoning gas (a reducing atmosphere) contained in exhaust gas.

The first pump cell 140C functions similarly to the oxygen pump cell 140 in that the first pump cell 140C pumps oxygen (so-called oxygen pumping) between the ambient atmosphere and a first measuring chamber 107c2, described below, via the second solid electrolyte body 109C.

The third electrode 108C and the fourth electrode 110C correspond to "a pair of electrodes" of the invention.

The oxygen-concentration determination cell 130C includes the first solid electrolyte body 105C and a first electrode 104C and a second electrode 106C formed respectively on the opposite surfaces of the first solid electrolyte body 105C. The oxygen-concentration determination cell 130C can generate an electromotive force according to the difference in partial pressure of oxygen between the first measuring chamber 107c2 and a reference oxygen chamber 170, which are separated from each other by the first solid electrolyte body 105C. The reference oxygen chamber 170 is described below.

The first measuring chamber 107c2, which is a small hollow space, is formed between the second solid electrolyte body 109C and the first solid electrolyte body 105C. The second electrode 106C and the third electrode 108C are disposed within the first measuring chamber 107c2. The first measuring chamber 107c2 is a small space of the gas sensor element 100C into which a gas-to-be-measured from the ambient atmosphere is first introduced.

A porous first diffusion resistor 115C is disposed in the first measuring chamber 107c2 on a side toward the forward end of the gas sensor element 100C. The first diffusion resistor 115C intervenes between the first measuring chamber 107c2 and the ambient atmosphere and is adapted to adjust the diffusion rate of the gas-to-be-measured into the first measuring chamber 107c2.

Furthermore, a second diffusion resistor 117 is disposed in the first measuring chamber 107c2 on a side toward the rear end of the gas sensor element 100C. The second diffusion resistor 117 serves as a partition between the first measuring chamber 107c2 and an opening portion 181 connected to the second measuring chamber 160, described below, and is adapted to control diffusion of gas. The first electrode 104C and the second electrode 106C correspond to "a pair of electrodes" of the invention.

Furthermore, the gas sensor element 100C includes a second pump cell 150 composed of the third solid electrolyte body 151, a fifth electrode 152, and a sixth electrode 153. The third solid electrolyte body 151 is disposed so as to face the first solid electrolyte body 105C with the insulator 185 sandwiched therebetween. The insulator 185 is not disposed at the position where the fifth electrode 152 is formed, thereby forming the reference oxygen chamber 170 in the form of an independent space. The first electrode 104C of the oxygen-concentration determination cell 130C is also disposed in the reference oxygen chamber 170. The reference oxygen chamber 170 is filled with a ceramic porous body. Also, the insulator 185 is not disposed at the position where the sixth electrode 153 is formed, thereby forming the hollow second measuring chamber 160 in the form of an independent space in such a manner that the insulator 185 separates the reference oxygen chamber 170 and the second measuring chamber 160 from each other. The first solid electrolyte body 105C and the insulator 180 have opening portions 125 and 181, respectively, formed so as to communicate with the second measuring chamber 160. Thus, as mentioned above, the first measuring chamber 107c2 and the opening portion 181 are connected to each other with the second diffusion resistor 117 intervening therebetween.

The second pump cell 150 can pump oxygen between the reference oxygen chamber 170 and the second measuring chamber 160, which are separated from each other by the insulator 185.

The fifth electrode 152 and the sixth electrode 153 correspond to "a pair of electrodes" of the invention.

The inner porous layer 21C is provided directly on the surface of a laminate of the detection element 300C and the heater 200C, and the outer porous layer 23C is formed so as to cover the outer surface of the inner porous layer 21C. That is, a porous protection layer 20C (the inner porous layer 21C and the outer porous layer 23C) is provided so as to entirely cover a forward end portion of the gas sensor element 100C.

In the case of the gas sensor element 100C, which is an $NO_X$ sensor element, another measuring chamber (the second measuring chamber 160) communicates with the first measuring chamber 107c2 at the rear end of the first measuring chamber 107c2, and the sixth electrode 153 is provided on the second measuring chamber 160. Therefore, the porous protection layer 20C extends rearward beyond the rear end of the second measuring chamber 160 so as to cover at least the rear end of the sixth electrode 153.

Similar to the case of the first embodiment, the porous protection layer 20C completely covers four surfaces (i.e., the front and back surfaces and the opposite side surfaces) of the gas sensor element 100C (laminate).

Also in the second embodiment, by means of the outer porous layer 23C having a porosity lower than that of the inner porous layer 21C, the outer porous layer 23C having a reduced porosity effectively traps poisoning substances and water droplets, and thus poisoning substances and water are unlikely to reach the detection element 300C (the detection portion 150C). In addition, by means of the inner porous layer 21C having a porosity higher than that of the outer porous layer 23C, the total volume of voids (empty spaces) contained in the inner porous layer 21C is increased, thereby imparting a thermal insulation property to the inner porous layer 21C. Therefore, even when the outer porous layer 23C is cooled by adhesion of water, the inner detection portion 150C is unlikely to be suddenly cooled. Even in a state where the detection portion 150C is heated by means of the heater 200C, damage to the gas sensor element 100C caused by adhesion of water can be effectively suppressed.

Since the inner porous layer 21C contains, as main components, the aforementioned ceramic particles and ceramic fiber filaments which are mainly formed of a ceramic material, the strength of the inner porous layer 21C can be improved. In addition, unlike the case where the inner porous layer 21C is formed only from fine particles, cracking in the inner porous layer 21C can be prevented, which would otherwise occur due to separation of bonded fine particles by surface tension.

Next, operation of the $NO_X$ sensor element 100C for determining $NO_X$ concentration will be briefly described. Firstly, the first pump cell 140C pumps oxygen out of the first measuring chamber 107c2 to the ambient atmosphere or pumps oxygen into the first measuring chamber 107c2 from the ambient atmosphere so as to maintain the potential difference between the electrodes 104C and 106C at a fixed level near 425 mV.

Exhaust gas whose oxygen concentration is adjusted in the first measuring chamber 107c2 as described above is introduced into the second measuring chamber 160 via the second gas diffusion layer 117. $NO_X$ contained in the exhaust gas comes into contact with the sixth electrode 153 in the second measuring chamber 160 and is decomposed (reduced) into $N_2$ and $O_2$ by the catalytic effect of the sixth electrode 153. Oxygen generated through decomposition receives electrons from the sixth electrode 153 to become oxygen ions. The oxygen ions flow through the third solid electrolyte layer 151 to the fifth electrode 152. At this time, residual oxygen which has not been pumped out from the first measurement chamber 107c2 similarly moves into the reference oxygen chamber 170 through the Ip2 cell 150. Thus, the current flowing through the Ip2 cell 150 consists of current stemming from decomposition of $NO_X$ and current stemming from decomposition of residual oxygen.

Since the residual oxygen which has been pumped out of the first measurement chamber 107c2 is adjusted to a predetermined concentration as described above, current due to decomposition of the residual oxygen can be considered substantially constant. Thus, the effect of the residual oxygen on variation in current stemming from decomposition of $NO_X$ is small. Therefore, current flowing through the Ip2 cell 150 is proportional to $NO_X$ concentration.

The present invention is not limited to the above-described embodiments, but is applicable to any gas sensor (gas sensor element) which includes a detection portion having a solid electrolyte body and a pair of electrodes. The present invention is applied to an oxygen sensor (oxygen sensor element) and an $NO_X$ sensor ($NO_X$ sensor element) in the above-described embodiments, but application of the present invention is not limited thereto. Needless to say, the present invention may encompass various modifications and equivalents thereof without departing from the spirit and scope of the claims appended hereto. For example, the present invention may be applied to an HC sensor (HC sensor element) for determining HC concentration.

EXAMPLES

A gas sensor element of Example 1 will now be described.

As described below, slurry A to be formed into an inner porous layer 21 was prepared so as to have an appropriate viscosity. The thus-prepared slurry A was applied, by dipping, to the surfaces (front and back surfaces and opposite side surfaces) of a forward end portion of a plate-like gas sensor element (wide-range air-fuel ratio sensor element) 100 shown in FIGS. 1 to 4 so as to achieve a coating thickness of 200 μm. Thereafter, in order to volatilize excess organic solvent contained in slurry A, the slurry-coated gas sensor element was dried for several hours using a drier set at 200° C., followed by firing in air at 1,100° C. for three hours for forming the inner porous layer 21.

Slurry A was prepared as follows: alumina particles (mean particle size: 0.1 μm) and alumina fiber filaments (mean fiber length: 100 μm) (total amount of the particles and the fiber filaments: 40 vol %), carbon powder (mean particle size: 20.0 μm) (60 vol %), and alumina sol (external incorporation) (10 wt. %) were weighed; ethanol was added to these materials; and the resultant mixture was stirred. The amounts of alumina powder and alumina fiber filaments in slurry A were varied as shown in Table 1. The mean particle size was determined by laser diffraction scattering. The mean fiber length of alumina fiber filaments was determined by measuring the length of each filament before mixing of the filaments for preparation of slurry A, and averaging the thus-measured lengths.

In the present Example, the only components remaining after sintering are the ceramic particles (alumina particles) and the ceramic fiber filaments (alumina filaments). Thus, virtually no difference is observed between the mean fiber length of the alumina fiber filaments measured during mixing for preparation of slurry A and after sintering, or between the total amount of the alumina particles and the alumina fiber filaments measured during mixing for preparation of slurry A and after sintering. Therefore, the mean fiber length of the alumina fiber filaments and the total amount of the alumina particles and the alumina fiber filaments measured during mixing for preparation of slurry A were taken as corresponding to those in the inner porous layer 21 formed through sintering.

After applying slurry A to the surface of the gas sensor element 100, the gas sensor element 100 was visually observed during drying and after firing for determining whether or not cracking had occurred in the inner porous layer 21. The results are shown in Table 1.

TABLE 1

| Slurry No. | Amount of alumina particles (vol %) | Amount of alumina fiber filaments (vol %) | Mean fiber length of alumina fiber filaments (μm) | Presence or absence of cracking after drying | Presence or absence of cracking after firing |
|---|---|---|---|---|---|
| A1 | 100 | 0 | 100 | Presence | Not observed |
| A2 | 87.5 | 12.5 | 100 | Presence | Not observed |
| A3 | 75 | 25 | 100 | Absence | Absence |
| A4 | 50 | 50 | 100 | Absence | Absence |
| A5 | 25 | 75 | 100 | Absence | Absence |
| A6 | 20 | 80 | 100 | Absence | Presence |

As seen from Table 1, in the case of employing any of slurries A3 to A5, in which the alumina fiber content of slurry A was 25 to 75 vol %, cracking did not occur in the layer during drying and after firing.

In contrast, in the case of employing slurry A1 or slurry A2, in which the alumina fiber content of slurry A was less than 25 vol %, cracking occurred in the layer during drying.

In the case of employing slurry A6, in which the alumina fiber content of slurry A exceeded 75 vol %, cracking did not occur in the layer during drying, but cracking occurred in the layer after firing. Conceivably, this is attributed to the fact that an excessively large amount of alumina fiber filaments in the layer inhibits sintering of alumina particles (interparticle bonding).

A gas sensor element of Example 2 will now be described.

As described below, slurry B to be formed into an inner porous layer 21 was prepared so as to have an appropriate viscosity. The thus-prepared slurry B was applied, by dipping, to the surfaces (front and back surfaces and opposite side surfaces) of a forward end portion of a plate-like gas sensor element (wide-range air-fuel ratio sensor element) 100 shown in FIGS. 1 to 4 so as to achieve a coating thickness of 200 μm. Thereafter, in order to volatilize excess organic solvent contained in slurry B, the slurry-coated gas sensor element was dried for several hours using a drier set at 200° C.

Subsequently, slurry C to be formed into an outer porous layer 23 was prepared so as to have an appropriate viscosity. The thus-prepared slurry C was applied, by dipping, to the surface of the inner porous layer 21 so as to achieve a coating thickness of 200 μm. Thereafter, in order to volatilize excess organic solvent contained in slurry C, the slurry-coated gas sensor element was dried for several hours using a drier set at 200° C., followed by firing in air at 1,100° C. for three hours for forming the outer porous layer 23 on the inner porous layer 21.

Slurry B was prepared as follows: alumina particles (mean particle size: 0.1 μm) (20 vol %), alumina fiber filaments (20 vol %), carbon powder (mean particle size: 20.0 μm) (60 vol %), and alumina sol (external incorporation) (10 wt. %) were weighed; ethanol was added to these materials; and the resultant mixture was stirred. The mean fiber length of alumina fiber filaments in slurry B was varied as shown in Table 2. The mean particle size was determined by laser diffraction scattering. Similar to the case of Example 1, the mean fiber length of the alumina fiber filaments and the total amount of the alumina particles and the alumina fiber filaments measured during mixing for preparation of slurry B were regarded as corresponding to those in the inner porous layer 21 formed by sintering.

Slurry C was prepared as follows: alumina particles (mean particle size: 0.1 μm) (40 vol %), spinel particles (mean particle size: 40 μm) (60 vol %), and alumina sol (external incorporation) (10 wt. %) were weighed; ethanol was added to these materials; and the resultant mixture was stirred. The mean particle size was determined by laser diffraction scattering.

The resultant gas sensor element 100 was subjected to vibration by means of an ultrasonic generator for three minutes while the gas sensor element 100 was immersed in water. After completing this test, the porous protection layer 20 was visually observed for determining whether or not any damage (exfoliation or cracking) had occurred. The results are shown in Table 2. When cracking occurs in the inner porous layer 21 or the inner porous layer 21 is removed from the gas sensor element, the outer porous layer 23 formed on the inner porous layer 21 is also removed from the gas sensor element. Namely, in those instances, damage occurs in the entire porous protection layer 20.

TABLE 2

| Slurry No. | Amount of alumina particles (vol %) | Amount of alumina fiber filaments (vol %) | Mean fiber length of alumina fiber filaments (μm) | Presence or absence of damage to porous protection layer |
|---|---|---|---|---|
| B1 | 50 | 50 | 20 | Presence |
| B2 | 50 | 50 | 50 | Presence |
| B3 | 50 | 50 | 70 | Absence |
| B4 | 50 | 50 | 100 | Absence |
| B5 | 50 | 50 | 200 | Absence |
| B6 | 50 | 50 | 300 | Presence |

As seen from Table 2, in the case of employing any of slurries B3 to B5, in which the mean fiber length of alumina fiber filaments was 70 to 200 μm, no damage occurred in the porous protection layer 20.

In contrast, in the case of employing slurry B1 or B2, in which the mean fiber length of alumina fiber filaments contained in slurry B was less than 70 μm, damage occurred in the porous protection layer 20. Conceivably, this is attributed to the fact that excessively short alumina fiber filaments insufficiently reinforce the inner porous layer 21.

Also in the case of employing slurry B6, in which the mean fiber length of alumina fiber filaments contained in slurry B exceeded 200 μm, damage occurred in the porous protection layer 20. Conceivably, this is attributed to the fact that excessively long alumina fiber filaments inhibit sintering of alumina particles (interparticle bonding) in the inner porous layer 21.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-249600 filed Nov. 13, 2012, incorporated herein by reference in its entirety.

What is claimed is:

1. A gas sensor element comprising:
    a detection portion including a solid electrolyte body, and a pair of electrodes disposed on the solid electrolyte body; and
    a porous protection layer covering the detection portion, wherein the porous protection layer comprises an inner porous layer provided over the detection portion, and an outer porous layer formed externally of the inner porous layer; the inner porous layer has a higher porosity than the outer porous layer; the inner porous layer contains, as main components, ceramic particles, and ceramic fiber filaments which are mainly formed of a ceramic material and which have a mean fiber length of 70 to 200 μm; and the amount of the ceramic fiber filaments is 25 to 75 vol % based on the total amount of the ceramic particles and the ceramic fiber filaments contained in the inner porous layer, the total amount taken as 100 vol %.

2. A gas sensor comprising the gas sensor element as claimed in claim 1 for determining the concentration of a particular gas component in a gas-to-be-measured, and a housing for holding the sensor element.

* * * * *